United States Patent

Fletcher et al.

[11] Patent Number: 5,939,056
[45] Date of Patent: Aug. 17, 1999

[54] UNDERARM COMPOSITION

[75] Inventors: Neil Robert Fletcher, Irby; Lynda Grainger, Hoole; Desmond Bernard Hagan, York; Nina Maria Lewkowicz, Meols; Ian Robert McMillan, Liverpool; John Harold Stewart Rennie, Chester, all of United Kingdom

[73] Assignee: Helene Curtis, Inc., Chicago, Ill.

[21] Appl. No.: 08/923,598

[22] Filed: Sep. 4, 1997

[30] Foreign Application Priority Data

Sep. 4, 1996 [GB] United Kingdom ............ 9618426

[51] Int. Cl.$^6$ .............. A61K 7/32; A61K 7/00; A61K 33/04
[52] U.S. Cl. ................... 424/65; 424/66; 424/67; 424/68; 424/400; 424/401; 424/703; 424/704
[58] Field of Search .................. 424/65, 66, 67, 424/68, 400, 401, 703, 704

[56] References Cited

U.S. PATENT DOCUMENTS

| | | |
|---|---|---|
| 5,225,188 | 7/1993 | Abrutyn et al. ............... 424/66 |
| 5,298,236 | 3/1994 | Orr et al. ............... 424/65 X |
| 5,338,536 | 8/1994 | Thimineur et al. ............... 528/10 |
| 5,397,566 | 3/1995 | Thimineur et al. ............... 424/70.12 |
| 5,541,276 | 7/1996 | Thimineur et al. ............... 424/70.1 |

FOREIGN PATENT DOCUMENTS

| | | |
|---|---|---|
| 028853 | 5/1981 | European Pat. Off. . |
| 135315 | 3/1985 | European Pat. Off. . |
| 549223 | 6/1993 | European Pat. Off. . |

*Primary Examiner*—Shelley A. Dodson
*Attorney, Agent, or Firm*—Matthew Boxer

[57] ABSTRACT

A substantially anhydrous underarm cream composition suitable for topical application to the human skin, comprising an antiperspirant and/or deodorant agent, a carrier, a silica structurant and an alkyl methicone wax having the general formula:

$$(CH_3)_3Si-[O-Si(R)(CH_3)]_x-O-Si(CH_3)_3$$

wherein R is a branched or unbranched alkyl group containing from 12 to 26 carbon atoms, the ratio of branched to unbranched alkyl groups is approximately from 1:5 to 1:2 and x ranges from 30 to 150.

15 Claims, 2 Drawing Sheets

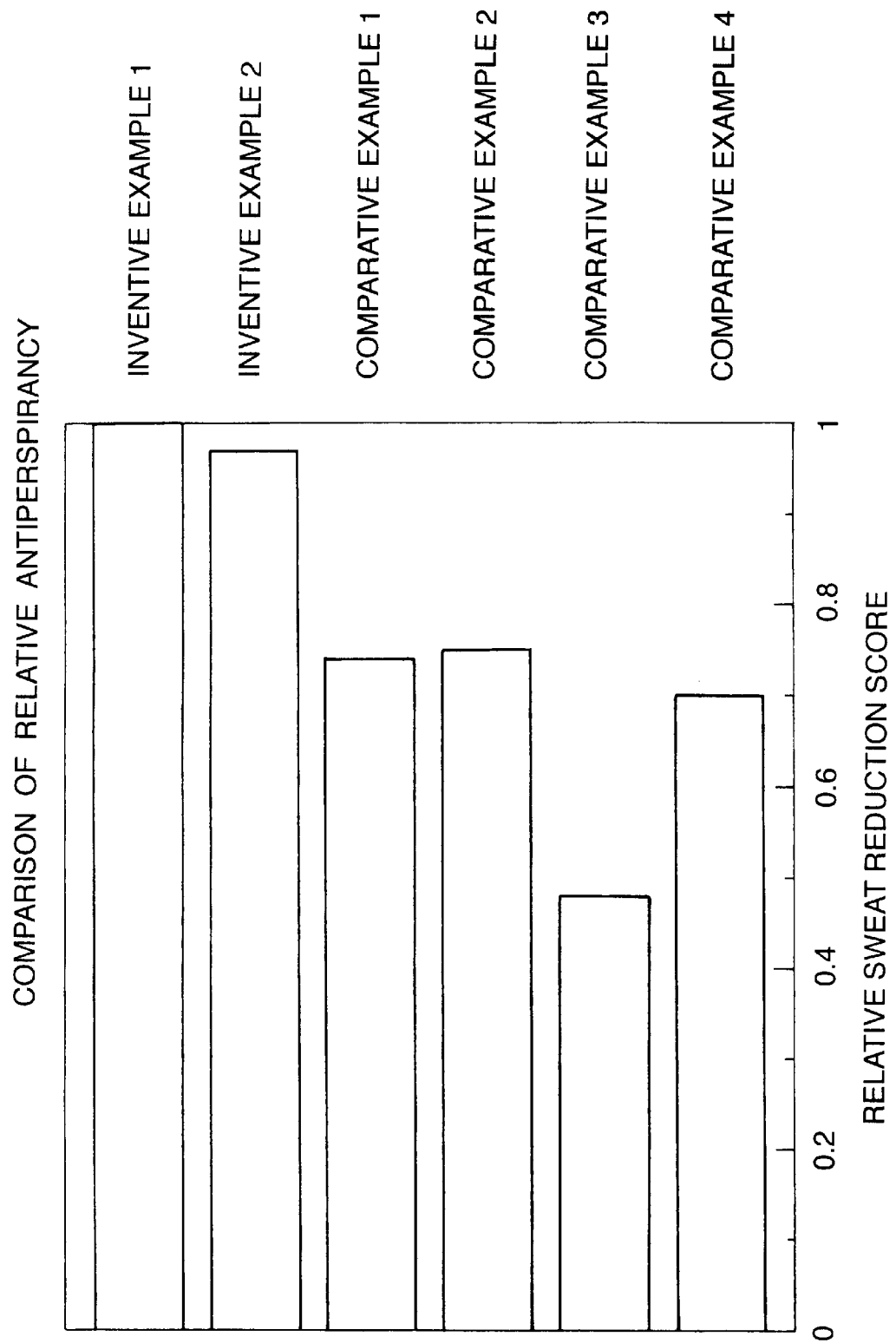

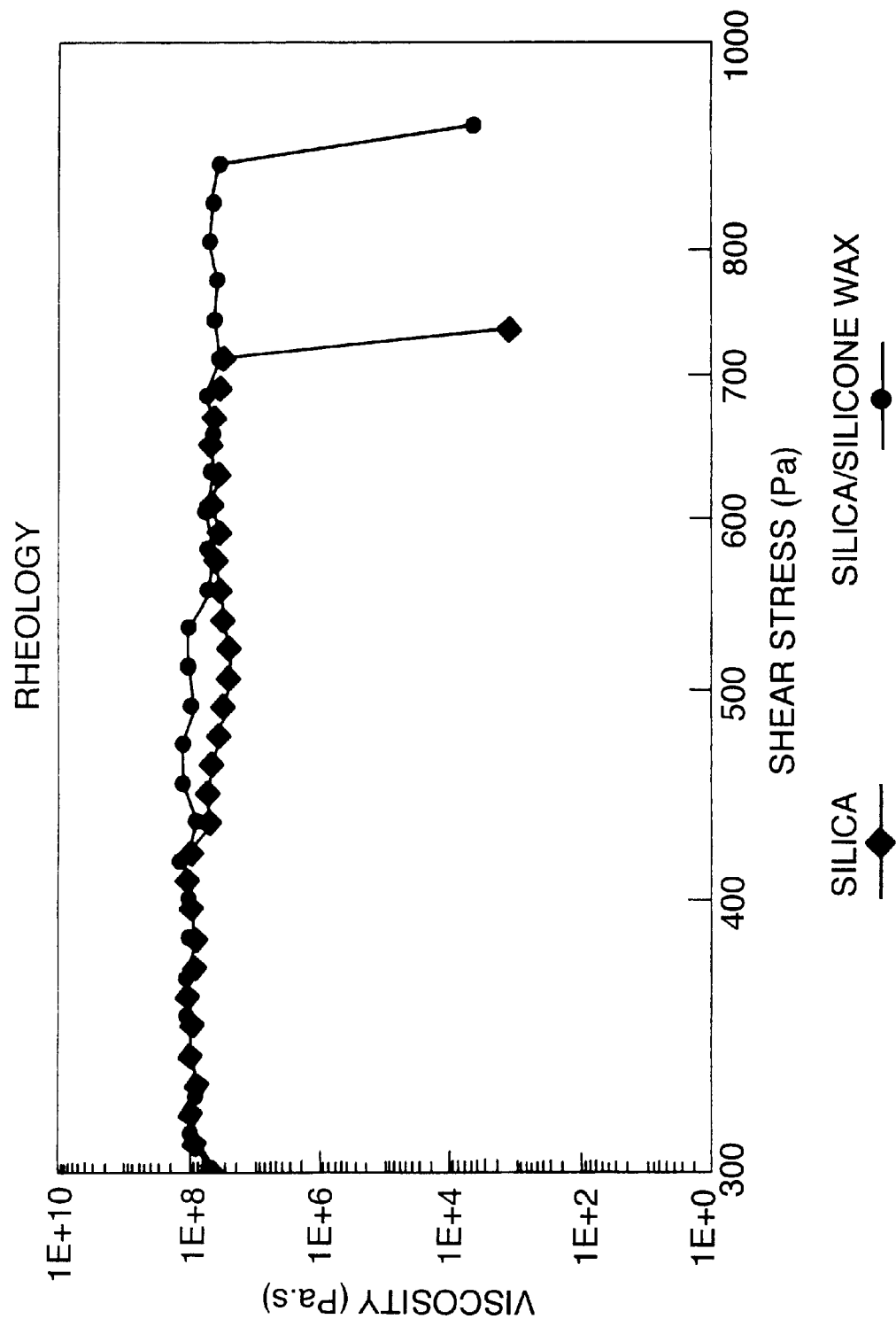

UNDERARM COMPOSITION

The invention relates to novel cream underarm compositions. More particularly, the invention concerns antiperspirant and deodorant compositions having improved efficacy containing a structurant and a wax.

It is known for underarm compositions for topical application to contain non-volatile silicone fluids such as polyorganosiloxanes which impart emolliency to the composition and can provide a masking effect to conceal solids present in the composition. Examples of such solids include antiperspirant actives. The efficacy of the composition is not seriously affected by the presence of the non-volatile silicone. Examples of such compositions are to be found in EP 28853 (The Procter & Gamble Company).

It is also known to include certain categories of alkyl siloxane waxes in underarm compositions. EP 549223 (Dow Corning) describes stick, roll on and spray underarm compositions containing certain long chain alkyl silicone waxes. The waxes are alleged to provide the formulations with desirable characteristics such as improved hardness, reduced whitening, improved skin feel and compatibility with other ingredients.

EP 135315 (The Mennen Company) describes a clay free antiperspirant product containing a volatile silicone and a gelling agent.

U.S. Pat. No. 5,541,276 (Thimineur), U.S. Pat. No. 5,397,566 (Thimineur) and U.S. Pat. No. 5,338,536 (Thimineur) all describe polyalkyl siloxane copolymers.

However, it has been found that wax structured cream compositions, whilst enjoying sensory and other benefits, can suffer from impaired efficacy—the antiperspirant particles are suspended between wax bridges and it is believed that the wax structurant coats the antiperspirant active particles with a layer of wax.

An object of the invention is to provide a cream underarm composition having improved efficacy and desirable sensory and rheological properties.

For the purposes of the present invention a cream can be described as having a cone penetration value of between approximately 10 mm and 30 mm where the cone has a diameter of 16.5 mm and a weight of 102.5 g.

Surprisingly, it has now been found that by selecting a class of structurant and polyalkylmethylsiloxane waxes having defined alkyl group characteristics an underarm composition having improved efficacy and desirable sensory and rheological properties is obtained.

According to the invention there is provided a substantially anhydrous underarm cream composition suitable for topical application to the human skin, comprising an antiperspirant and/or deodorant agent, a carrier, a silica structurant and a polyalkylmethylsiloxane wax having the general formula:

$(CH_3)_3Si$—$[O$—$Si(R_1)(CH_3)]_y$—$[O$—$Si(R_2)(CH_3)]_z$—$O$—$Si(CH_3)_3$, wherein $R_1$ is a straight chain alkyl group containing from 14 to 22 carbon atoms, $R_2$ is a branched alkyl group containing from 14 to 22 carbon atoms, y+z is from 50 to 80 and z/(y+z) ranges from 0.25 to 0.4.

Preferably the wax according to the invention is of the general formula:

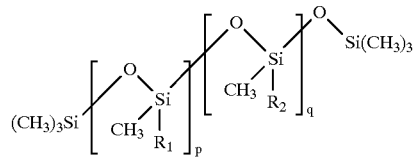

where $R_1$ is a linear alkyl group, $R_2$ is a branched alkyl group, q/(p+q) is approximately 0.32, the average alkyl chain length is from C16 to C18, and p+q=65.

Preferably, the composition comprises 3 to 20% by weight of the wax and more preferably 5 to 15% by weight. Suitably, the composition comprises 2 to 10%, preferably 3 to 7% by weight of silica.

Advantageously, the composition further comprises a non-volatile masking oil. The masking oil is selected from non-volatile silicones, polyolefins and mixtures thereof. Suitably, the polyolefin is polydecene and is present at 1 to 30% and preferably 5 to 20% by weight of the composition.

Preferably, the carrier is a carried fluid which is a volatile silicone and is present at 20 to 70%, preferably 30 to 60% by weight of the composition.

Although the applicants do not wish to be bound by any theory it is believed that the structuring effect of silica complements the structuring effect of the polyalkylmethyl silicone wax to provide a composition which is highly efficacious and has improved rheological properties. More particularly, silica structurants provide network structures consisting of interconnected flocs which are formed by aggregates interacting via silanol-silanol hydrogen bonding of silanol groups on the silica surface. The interlocking network is not generally as resistant to shear forces as other structures. However, it is believed that the combination of a silica and silicone wax structuring system in accordance with the invention provides an improved antiperspirant composition without compromising Theological or efficacy requirements of such compositions. Moreover, the efficacy inhibiting properties of silicone waxes when used alone are reduced.

Suitable antiperspirant salts include inorganic and organic salts of aluminium and zirconium and mixtures thereof. Particularly preferred are the aluminium/zirconium salts of aluminium halides, aluminium hydroxyhalides, aluminium zirconium salts and mixtures thereof. Particularly preferred antiperspirant salts include activated aluminium chlorohydrate compounds as described in EP6739 (Unilever NV et al). Further antiperspirant actives are described in EP 28853. The contents of both these applications are incorporated herein by reference.

Any effective deodorant composition known in the art is suitable for incorporation into the composition e.g. sodium bicarbonate, zinc ricinoleate, other inorganic salts, short chain monohydric alcohols, polyhydric alcohols or compounds such as triclosan. The deodorants can be utilised alone or in conjunction with the antiperspirant active component where compatible.

The carrier suitably comprises a volatile silicone material. Examples of such materials are cyclic or linear polydimethylsiloxanes. Preferred cyclic polydimethylsiloxanes have from 3–7 silicon atoms and a viscosity less than $10 \times 10^{-6} m^2 s^{-1}$ (cSt) at 25° C. Preferred linear polydimethylsiloxanes have from 3–9 silicon atoms and a viscosity of less than $5 \times 10^{-6} m^2 s^{-1}$ (cSt) at 25° C. Preferred polydimethylsiloxanes are available from Dow Corning Corporation as Dow Corning 344 and 345. Preferably, if used in the composition, the volatile silicone is present at a level of 30 to 60% by weight, more preferably 40 to 60% by weight.

The non-volatile masking agent is also present in the formulation and preferably comprises a hydrocarbon polymer such as polyolefins.

The polyolefins are suitably hydrocarbon polymers, with the preferred ones being liquid at room temperature (i.e. 21° C.). It is also highly preferred that the polyolefin in the composition has a relatively low viscosity. Preferably, the viscosity of the polyolefin hydrocarbon masking agent is less than about $40\times10^{-6}m^2\,s^{-1}$ (cSt) at 40° C., more preferably less than about $30\times10^{-6}m^2\,s^{-1}$ (cSt) at 40° C.

Preferably, the polyolefin comprises a polyalphaolefin. Preferred polyalphaolefins for use in compositions according to the invention are polydecenes, for example the Silkflo range of polydecenes, manufactured by Albermarle Corporation. Other preferred polyolefins for use in compositions according to the invention include polybutene, which is commercially available under the trade name Panalene L14E from Amoco, and polyisobutene, which can be obtained from Prespere under the trade name Permethyl.

As such, preferred polyolefins for use in compositions according to the invention may have monomer chain lengths in the region of 3–15 carbon atoms. Preferred polyolefin blends which are commercially available may conveniently contain a blend of various polymers, including dimers, trimers, and so on. Preferred materials for use in compositions according to the invention include Silkflo 362NF, Silkflo 364NF, and Silkflo 366NF, available from Albermarle Corporation.

When used in compositions according to the invention, the polyolefin hydrocarbons described help to confer good sensory properties on the composition, including a surprising lack of greasiness after application, and where the composition is an antiperspirant composition, provide a high degree of masking of any whiteness that may be left by the antiperspirant salt in the composition.

An advantage of using the polyolefin hydrocarbons is that they have been found not to interfere with the efficacy of any antiperspirant active salt in the composition to a significant degree.

The non-volatile masking oil which can function as an emollient can also be a non-volatile silicone. The non-volatile silicone may be a polyalkylsiloxane, a polyalkarylsiloxane or a polyethersiloxane copolymer. Preferred polyalkysiloxanes have viscosities ranging from 10 to $100,000\times10^{-6}m^2\,s^{-1}$ (cSt) at 25° C. Such siloxanes are available from the Dow Corning Corporation as the Dow Corning 200 series.

Suitable polyalkaryl siloxanes are the polymethylphenylsiloxanes having viscosities of 15 to $65\times10^{-6}m^2\,s^{-1}$ (cSt) at 25° C. These siloxanes are available as the Dow Corning 556 fluid.

A suitable polyether siloxane is dimethylpolyoxyalkylene ether copolymer having a approximate viscosity of 1200 to $1500\times10^{-6}\,m^2\,s^{-1}$ (cSt) at 25° C. e.g. a polysiloxane ethylene glycol ether copolymer.

The polyalkylmethylsiloxane waxes for use in the present invention have the general formula:

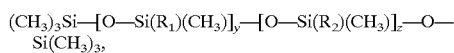

wherein $R_1$ is a straight chain alkyl group containing from 14 to 22 carbon atoms, $R_2$ is a branched alkyl group containing from 14 to 22 carbon atoms, y+z is from 50 to 80 and z/(y+z) ranges from 0.25 to 0.4.

Preferably the wax according to the invention is of the general formula:

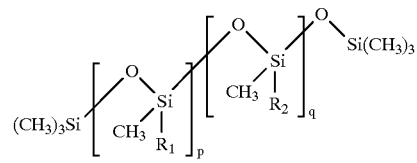

where $R_1$ is a linear alkyl group, $R_2$ is a branched alkyl group, q/(p+q) is approximately 0.32, the average alkyl chain length is from C16 to C18, and p+q=65.

The waxes have been found to enhance the smoothness and lubricity of the cream and do not inhibit efficacy. Moreover, a masking effect is also obtained. The polyalkylmethyl siloxane wax has a melting point of approximately 32 to 33° C.

Typically, the waxes are made up of a mixture of alkyl group chain lengths.

An essential feature of the compositions of the invention is the presence of a silica structurant such as colloidal silica materials. The silica is made up of high surface area micron to sub-micron sized silica particulates.

Preferably, the surface area is greater than $100m^2/gm$ of material.

Suitable colloidal silica materials are Syloid (available from W. R. Grace) and Cab-O-Sil (available from Cabot Corporation) Aerosil 200 (available from Degussa AG) is a particularly preferred colloidal silica.

Optional additional structurant waxy materials apart from those of the invention can also be incorporated into the underarm creams of the invention and include high and low melting point waxes, gums, resins, polymers, starches and elastomers. High melting point waxes include insect and animal waxes such as beeswax and spermaceti; vegetable waxes such as carnauba, candelilla, Ouricury, Japan wax, Douglasfir bark wax, rice-bran wax, castor wax and bayberry wax; mineral waxes such as montan wax, peat wax, ozokerite and ceresin; petroleum waxes such as paraffin wax; synthetic waxes such as Fischer-Tropsch waxes, polyethylene waxes, chemically modified hydrocarbon waxes and substituted amide waxes. Examples of low melting point waxy materials include fatty acids, fatty alcohols, fatty acid esters and fatty acid amides having carbon chains of 3 to 30 carbon atoms. Particularly preferred low melting point waxy materials include stearyl alcohol, cetyl alcohol, myristyl alcohol and palmitic acid.

In addition to the essential ingredients of the compositions of the invention one may also include therein minor amounts of components such as perfumes, colouring agents, whitening agents such as titanium dioxide, antioxidants, and ultra-voilet absorbers to enhance colour, improve aesthetic value and consumer acceptability. Minor amounts of other ingredients which do not effect the beneficial properties of the underarm compositions of the invention may also be included.

The invention will now be described having regard to the following non-limiting examples:

EXAMPLE

Examples IE1 and IE2 are examples according to the invention. Examples CE1 to CE4 are comparative examples

TABLE I

| INGREDIENT | IE1 | IE2 | CE1 | CE2 | CE3 | CE4 |
|---|---|---|---|---|---|---|
| Antiperspirant active | 24.00 | 24.00 | 24.00 | 24.00 | 24.00 | 24.00 |
| Talc | 6.00 | 6.00 | — | 5.00 | 6.00 | 6.00 |
| Fumed Silica | 4.00 | 4.00 | — | — | — | 4.00 |
| Polyalkylmethyl-siloxane | 6.00 | 6.00 | — | — | — | — |
| Masking oil | 10.00 | 10.00 | — | 37.50 | 10.00 | 10.00 |
| Fragrance | 0.70 | 1.00 | — | 1.00 | 1.00 | 0.70 |
| Non-volatile carrier | 49.16 | 48.00 | 66.00 | 25.00 | 48.50 | 53.30 |
| Detergent | 0.14 | — | — | — | — | — |
| Propylene Carbonate | — | 1.00 | — | — | — | — |
| Castorwax | — | — | 10.00 | 7.50 | 4.50 | — |
| Stearyl Alcohol | — | — | — | — | 5.00 | — |
| PEG-8 Distearate | — | — | — | — | 1.00 | — |
| Ozokerite Wax | — | — | — | — | — | 2.00 |

In the examples the non-volatile carrier is cyclomethicone, the detergent is Softanol 70 and the antiperspirant active is AZAG.

The liquid components of the compositions (cyclomethicone, polydecene, fragrance and Softanol) were mixed with the wax according to the invention in a side vessel. The mixture was heated to 45° C. with stirring until the polyalkylmethyl siloxane wax was fully melted and the mixture was homogenous. The powder contents (silica, antiperspirant active and talc) were charged into a main mixing vessel and stirred until the silica was evenly dispersed. The wax/liquid mixture was then added. The mixture was then mixed with high shear and discharged into a bulk container or into packs as required.

The efficacy of the composition of Examples IE1 and IE2 was compared with the efficacy of Comparative Examples CE1 to CE4. The method required measurement of the sweat reduction capacity of each formulation using absorbent pads held in the axillae of human volunteers seated in a hot room at 40% relative humidity and 40° C. The method is fully described in Antiperspirants & Deodorants, ed. K. Laden & C. B. Felger, Cosmetic Science & Technology Series, Vol. 7, 1988, Dekker, ch. 7, Clinical Evaluation of Antiperspirants, C. B. Felger & J. G. Rogers. The comparative antiperspirancy results of the samples in the example are shown in FIG. 1.

Rheology:

FIG. II illustrates the superior rheology of the silica/silicone wax structured composition of the invention in comparison with a similar composition structured with silica only.

The method utilized a Carri-Med Controlled Stress Rheometer CSL100 instrument (a controlled shear stress rheometer). A vane/cup measuring system was employed for the cream compositions. A mesh interior was fitted to the cup to ensure prevention of "wall slip". The experiments were carried out at 25° C. Equilibrium Flow experiments were conducted on fresh samples to obtain the exact flow properties of the sample. The sample was allowed to equilibrate at a fixed temperature (25° C.) for 1 hour before measurement.

The information obtained from the data was the equilibrium viscosity (Pa.s) which occurs under low shear stress and is the point at which a sample catastrophically fails—a lower equilibrium viscosity point being indicative of a more unstable sample.

As can be seen from FIG. II, the silica/silicone wax composition of the invention failed at a shear stress close to 1,000 Pa while the silica structured composition failed at approximately 750 Pa.

We claim:

1. A substantially anhydrous underarm cream composition suitable for topical application to the human skin, comprising an antiperspirant and/or deodorant agent, a carrier, a silica structurant and an alkyl methicone wax having the general formula:

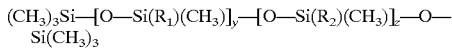

wherein $R_1$ is a straight chain alkyl group containing from 14 to 22 carbon atoms, $R_2$ is a branched alkyl group containing from 14 to 22 carbon atoms, y+z is from 50 to 80 and z/(y+z) ranges from 0.25 to 0.4.

2. An underarm composition according to claim 1 comprising a wax is of a general formula:

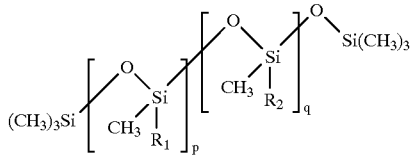

where $R_1$ is a linear alkyl group, $R_2$ is a branched alkyl group and, q/(p+q) is approximately 0.32, the average alkyl chain length is from C16 to C18, and p+q=65.

3. An underarm composition as claimed in claim 1 which comprises 3% to 20% by weight of the wax.

4. An underarm composition as claimed in claim 3 which comprises 5% to 15% by weight of the wax.

5. An underarm composition as claimed in claim 1 which comprises 2% to 10% by weight silica.

6. An underarm composition as claimed in claim 5 which comprises 3% to 7% by weight silica.

7. An underarm composition as claimed in claim 1 which further comprises a non-volatile masking oil.

8. An underarm composition as claimed in claim 7 wherein the non-volatile masking oil is selected from the group consisting of non-volatile silicones, polyolefins and mixtures thereof.

9. An underarm composition as claimed in claim 8 wherein the polyolefin is polydecene.

10. An underarm composition as claimed in claim 9 which comprises 1 to 30% polydecene.

11. An underarm composition as claimed in claim 1 wherein carrier is a volatile silicone.

12. An underarm composition as claimed in claim 11 which comprises 20 to 70% volatile silicone.

13. An underarm composition as claimed in claim 1 wherein the antiperspirant agent is selected from the group consisting of an inorganic salt of aluminium, an organic salt of aluminium, an organic salt of zirconium, an inorganic salt of zirconium and mixtures thereof.

14. A substantially anhydrous underarm cream composition suitable for a topical application to the human skin, comprising an antiperspirant and/or deodorant agent, a carrier, a silica structurant such as colloidal silica and an having the general formula alkyl methicone wax $(CH_3)_3Si$—$[O$—$Si(R_1)$ $(CH_3)]y$—$[O$—$Si(R_2)(CH_3)]_2$—$O$—$Si(CH_3)_3$ wherein $R_1$ is a straight chain alkyl group containing from 14 to 22 carbon atoms, $R_2$ is a branched alkyl group containing from 14 to 22 carbon atoms, y+z is from 50 to 80 and z/(y+z) ranges from 0.25 to 0.4.

15. A composition in according with claim 14 wherein the colloidal silica is selected from the group consisting of Cab-O-Sil and Aerosil 200.

* * * * *